(12) United States Patent
Okamoto et al.

(10) Patent No.: US 6,994,955 B2
(45) Date of Patent: Feb. 7, 2006

(54) ASSAY METHOD OF A COMPLEX OF LIPOPROTEIN WITH HEMOGLOBIN OR HEMOGLOBIN ANALOG

(75) Inventors: Masashi Okamoto, Kyoto (JP); Hajime Nakano, Kyoto (JP)

(73) Assignee: Arkray, Inc., Kyoto (JP)

( * ) Notice: Subject to any disclaimer, the term of this patent is extended or adjusted under 35 U.S.C. 154(b) by 175 days.

(21) Appl. No.: 10/324,029

(22) Filed: Dec. 20, 2002

(65) Prior Publication Data

US 2003/0109050 A1 Jun. 12, 2003

Related U.S. Application Data

(62) Division of application No. 09/875,891, filed on Jun. 8, 2001, now Pat. No. 6,524,862.

(30) Foreign Application Priority Data

Jun. 9, 2000 (JP) .................................. P. 2000-213481

(51) Int. Cl.
*C12Q 1/00* (2006.01)

(52) U.S. Cl. ............................................ 435/4; 436/66
(58) Field of Classification Search .................... 435/4; 436/66, 67, 87
See application file for complete search history.

(56) References Cited

U.S. PATENT DOCUMENTS 5,744,318 A  4/1998  Founds et al.

6,524,862 B2 *  2/2003  Okamoto et al. ............. 436/71

FOREIGN PATENT DOCUMENTS

| EP | 0 448 072 A2 | 9/1991 |
| JP | 8-245421 | 9/1996 |
| JP | 8-313530 | 11/1996 |

OTHER PUBLICATIONS

Szebeni et al., "Interaction of Hemoglobin Derivatives with Liposomes. Membrane Cholesterol Protects Against the Changes of Hemoglobin." *Biochemistry*, vol. 27, No. 17, (1998). pp. 6425–6435.

Galina P. Gorbenko, "Resonance energy transfer study of hemoglobin and cytochrome c complexes with lipids," *Biochimica et Biophysica Acta*. vol. 1409, No. 1 Nov. 2, 1998 pp. 12–24.

Kim–In–Sook, "Inhibition of hemoglobin–induced low density lipoprotein oxidation by haptoglobin,"0 *Experimental & Molecular Medicine*, vol. 28, No. 2 (1996), pp. 89–94.

Evans et al., "Binding of Lipid to Protein in the Low Density Lipo Protein From the Hens Egg," *Biochimica Et Biophysica Acta*. vol. 164, No. 3 (1968). pp. 566–574.

* cited by examiner

*Primary Examiner*—Ralph Gitomer
(74) *Attorney, Agent, or Firm*—Sughrue Mion, PLLC

(57) ABSTRACT

A selective complex of a lipoprotein with hemoglobin or a hemoglobin analogue; a method of assaying hemoglobin or a hemoglobin analogue in a sample, comprising reacting the sample with a lipoprotein which is capable of selectively forming a complex with hemoglobin or a hemoglobin analogue; and a kit for assaying hemoglobin or a hemoglobin analogue, comprising a lipoprotein which is capable of selectively forming a complex with hemoglobin or a hemoglobin analogue.

7 Claims, 2 Drawing Sheets

ASSAY METHOD OF A COMPLEX OF LIPOPROTEIN WITH HEMOGLOBIN OR HEMOGLOBIN ANALOG

This is a divisional of application Ser. No. 09/875,891 filed Jun. 8, 2001, the disclosure of which is incorporated herein by reference, now issued as U.S. Pat. No. 6,524,862.

BACKGROUND OF THE INVENTION

1. Filed of the Invention

The present invention relates to a selective complex of a lipoprotein with hemoglobin or a hemoglobin analogue; a method of assaying hemoglobin or a hemoglobin analogue in a sample, using the selective complex, and a kit for assaying hemoglobin or a hemoglobin analogue, using the selective complex in clinical examinations.

2. Discussion of the Background Art

In clinical examinations, it is required to selectively assay a target substance from a sample containing various coexisting substances. Accordingly, there have been employed a number of substances that specifically binds to target substances to form a pair just like a key and a keyhole, for example, antigen (including hapten)-antibody, ligand-receptor, substrate-enzyme, inhibitor-enzyme, or the like.

For example, the sandwich method is an immunoassay method using antibodies which is frequently employed. In this method, an antigen to be assayed is sandwiched between two kinds of antibodies. One of these antibodies is immobilized on a solid phase for capturing the antigen, while the other antibody is labeled. Then, the antigen to be assayed is allowed to react with the antibodies to thereby form a sandwich complex of immobilized antibody-antigen-labeled antibody. After removing the unreacted labeled antibody, the amount of the antigen is determined by measuring the label.

However, it generally takes much labor and costs a great deal to construct these antibodies, receptors, enzymes, and the like. In addition, some of them contain hardly available materials.

In clinical examinations relating to hemoglobin or hemoglobin analogues, the situation is similar. That is to say, substances having a specific affinity for hemoglobin (for example, haptoglobin) suffer from problems in cost and stable supply.

SUMMARY OF THE INVENTION

An object of the present invention is to provide a selective complex of a lipoprotein with hemoglobin or a hemoglobin analogue using materials which can be economically and stably supplied.

Another object of the present invention is to provide a method and a kit for assaying hemoglobin or a hemoglobin analogue, using the selective complex.

These and other objects of the present invention have been achieved by a selective complex of a lipoprotein with hemoglobin or a hemoglobin analogue.

Furthermore, these and other objects of the present invention have been achieved by a method of assaying hemoglobin or a hemoglobin analogue, comprising using the above selective complex.

Moreover, these and other objects of the present invention have been achieved by a kit for assaying hemoglobin or a hemoglobin analogue, comprising a lipoprotein which is capable of selectively forming a complex with hemoglobin or a hemoglobin analogue.

BRIER EXPLANATION OF THE DRAWINGS

DETAILED DESCRIPTION OF THE INVENTION

Figure 1:
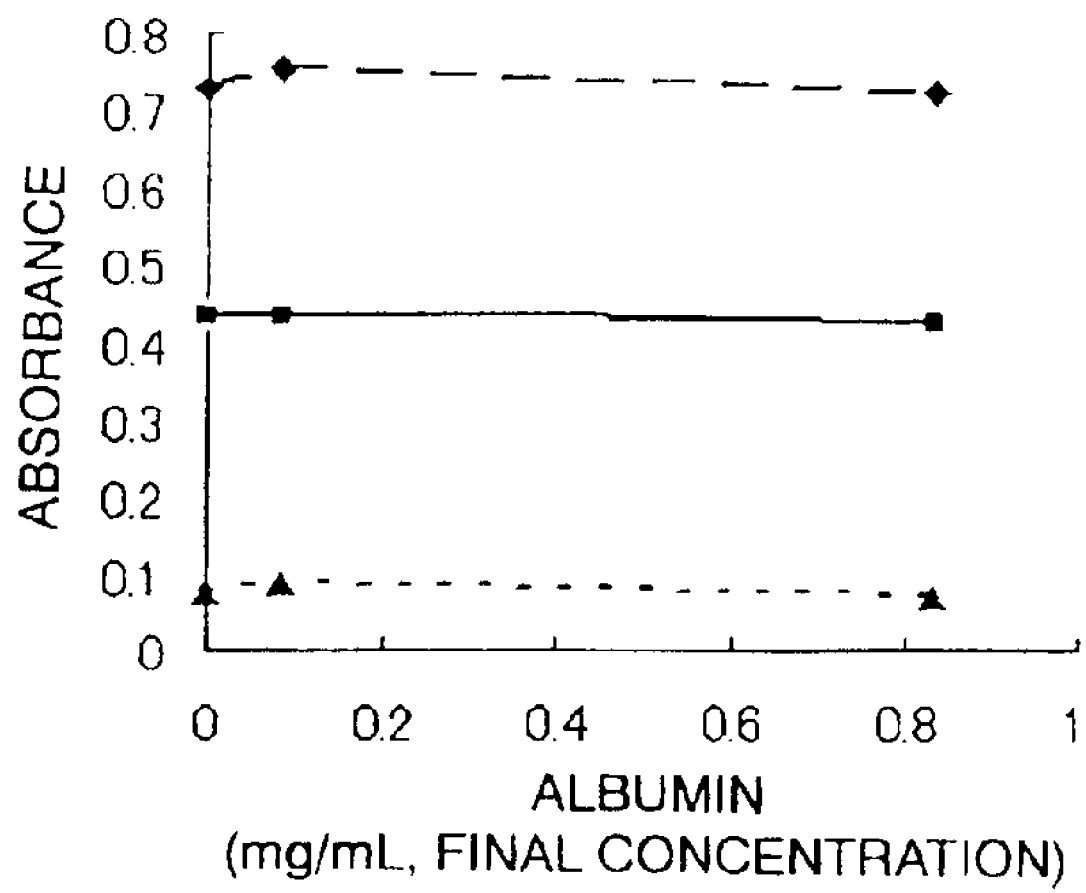
FIG. 1 is a graph showing absorbances measured, using a blue latex-labeled anti-$A_{1c}$ antibody, in the reactions of a casein-derived immobilized lipoprotein film with glycohemoglobin control levels I and II and bovine hemoglobin in the coexistence or absence of human serum albumin at different concentrations.

The inventors have conducted intensive studies on the binding properties of hemoglobin or hemoglobin analogues, and consequently found that a lipoproteins selectively binds to hemoglobin or a hemoglobin analogue to form a complex. They have further confirmed that this selective complex is applicable to clinical examinations and developed a method for assaying hemoglobin or a hemoglobin analogue without using an antibody, haptoglobin, or the like, thereby completing the present invention. Now, the present invention will be described in greater detail.

The "lipoprotein" for use in the present invention comprises a lipid and a protein, wherein at least a part of the protein forms a complex together with the lipid. The lipoprotein involves natural lipoproteins and lipoproteins obtained by artificially combining a lipid with a protein.

The lipid in the lipoprotein may be either a single lipid or a mixture, and either a natural product-derived lipid, a synthetic lipid or a mixture thereof, so long as it is dispersible in an aqueous system in the coexistence of a protein. Taking the temperatures from dispersion to use into consideration, it is preferred to use a lipid containing fatty acid side chains differing from each other in carbon atom number or unsaturation degree which is dispersible in the coexistence of a protein within the temperature range.

Examples of the natural product-derived lipid include vegetable fats, such as olive oil, linseed oil, coconut oil, and the like, and animal fats, such as lipids derived from chick yolk or cow's milk. In the present invention, a lipid comprising a triglyceride as a main component is preferred because it is less expensive and highly available.

It is also possible to use a lipid extracted from a specimen containing a protein. Examples thereof include lipids extracted from milk products, liquids extracted from casein specimens, and the like. The lipid can be extracted from such a specimen containing a protein by a method conventionally used in the art.

The protein component in the lipoprotein may be any protein so long as at least a part thereof can form a complex with the lipid to thereby make the lipid dispersible. The protein may be a natural lipoprotein or a protein either almost all of the components or a part of which can form a complex with the lipid. It is also possible to use a mixture thereof.

Among the protein components in the lipoprotein, preferred examples include a peripheral protein weakly interacting with a lipid, or a protein which is generally regarded as a soluble protein but weakly interacts with a lipid. Examples of the latter protein include casein, bovine serum albumin, and the like, and they are favorable from the viewpoints of cost and supply too.

In the present invention, the lipoprotein can be dispersed in an aqueous system by any method, such as a manual dispersion method, a mechanical dispersion method, an ultrasonic dispersion method or the like. It is also preferred to disperse the lipoprotein by elevating temperature. The ratio of the lipid to the protein in the dispersion step can be varied depending on the purpose. Also, the ratio may be varied depending on the kinds of the lipid and protein employed. The lipoprotein dispersion thus obtained is usually a colorless and transparent or milky liquid.

The lipoprotein dispersion prepared in the above may be used as a liquid system as such. Alternatively, it may be bonded to a solid phase. Namely, an appropriate form may be selected depending on the purpose. Examples of the solid phase include a porous film, such as a nitrocellulose film, and the like.

The lipoprotein dispersion may be bonded to the solid phase either via physical adsorption or chemical bond. The lipoprotein bonded to the solid phase is called "the immobilized lipoprotein" hereinafter.

The hemoglobin or hemoglobin analogue for use in the present invention include hemoglobin and hemoglobin derivatives, such as normal hemoglobin, abnormal hemoglobin, glycohemoglobin, acetylhemoglobin, and the like, as well as myoglobin, which is considered as a monomer of hemoglobin, and derivatives thereof.

In the method of assaying hemoglobin or a hemoglobin analogue according to the present invention, for example, a sample to be assayed is allowed to react with a lipoprotein which is capable of selectively forming a complex with hemoglobin or a hemoglobin analogue.

The complex which has been formed by binding the hemoglobin or hemoglobin analogue to the lipoprotein or immobilized lipoprotein can be confirmed or assayed by an assay method generally used in the art, for example, a method using the physicochemical properties (absorbance, etc.) of the hemoglobin or hemoglobin analogue, or a method wherein one of the constitutive components is labeled. In the labeling method, the target may be labeled with a label either directly or indirectly via an antibody or the like. Examples of the label include an enzyme, a dye, a radioactive material, and the like.

The assay method in which a selective complex according to the present invention is formed is particularly useful in clinical examinations. This method is applicable to external diagnosis as described below. On the other hand, it is also expected that this method is applicable to internal diagnosis wherein, for example, hemoglobin labeled with a radioisotope is introduced into the body and bonded to lipoprotein in the site of arteriosclerosis for imaging.

As an important example of the application of this assay method to external diagnosis, the assay of human hemoglobin $A_{1c}$ is exemplified. When a specimen which may contain human hemoglobin $A_{1c}$ is added to an immobilized lipoprotein, hemoglobin and hemoglobin $A_{1c}$, which is its derivative, are bonded to the immobilized lipoprotein at the same ratio. Then, a labeled anti-human hemoglobin $A_{1c}$ antibody is added thereto and allowed to react. After washing off the unbonded matters, the human hemoglobin $A_{1c}$ bonded to the immobilized lipoprotein is quantified based on the amount of the labeled substance. At this time, if the total hemoglobin content in the specimen is separately determined, the content (%) of human hemoglobin $A_{1c}$ can be determined from the hemoglobin $A_{1c}$ content and the total hemoglobin content.

More preferably, if the amount of the total hemoglobin which is bonded to the immobilized lipoprotein is constant, the human hemoglobin $A_{1c}$ content (%) can be determined without measuring the total hemoglobin content each time.

In the method and kit of the present invention, a carrier, an additive and/or a diluent can be used so long as they have no influence on the assay.

According to the present invention, assay in clinical examinations can be carried out using the selective complex of a lipoprotein with hemoglobin or a hemoglobin analogue. Moreover, the assay can be carried out using materials which are less expensive and can be supplied stably, without using any expensive material, such as an antibody or the like.

The present invention will be illustrated in greater detail by reference to the following Examples. However, it is to be understood that the present invention is not construed as being restricted thereto.

EXAMPLE 1

Construction of Immobilized Lipoprotein:

According to the method of Evans et al. (R. J. Evans, S. L. Bandemer, J. A. Davidson, K. Heinlein, S. S. Vaghefi, *Biochim. Biophys. Acta.*, 164: 566 (1968)), yolk lipoprotein LDF (Low Density Fraction) was extracted. A nitrocellulose film (manufactured by Millipore, pore size: 8 μm) was immersed in the resulting yolk lipoprotein solution, and the yolk lipoprotein was adsorbed on the film for blocking, followed by washing and drying to prepare an immobilized lipoprotein film. As a control, the nitrocellulose film was treated in the same manner, except for using a yolk lipoprotein-free solution. Binding of $^{125}$I-labeled hemoglobin to immobilized lipoprotein:

Hemoglobin was labeled with $^{125}$I by the chloramine-T method. Then, the $^{125}$I-labeled hemoglobin solution was allowed to react with the immobilized lipoprotein film and the control film.

Three minutes thereafter, each reaction system was washed and the $^{125}$I-labeled hemoglobin remaining on the film was measured with a gamma counter (ARC-1000 M, manufactured by Aloka Co., Ltd.). The immobilized lipoprotein film showed a radioactivity of 10,960 cpm, while the control film showed a radioactivity of 872 cpm. These results indicate that an apparently larger amount of the $^{125}$I-labeled hemoglobin bonded to the immobilized lipoprotein film than the control film.

EXAMPLE 2

(1) Extraction of Lipid from Casein

From 500 g of cow's milk casein (manufactured by Nacalai Tesque, Inc., CP Grade), lipids were extracted with a mixture of 500 ml of methanol with 1,000 ml of chloroform to give 2.7 g of a lipid extract.

(2) Construction of Immobilized Lipoprotein Film

To the lipid extract, an aqueous casein solution was added and dispersed with an ultrasonic homogenizer (UH-50, manufactured by Iuchi Seieido Co., Ltd.) to give a lipoprotein dispersion in a light milky color. A nitrocellulose film (manufactured by Millipore Corporation, pore size: 8 μm) was immersed in the dispersion, and the lipoprotein was adsorbed on the film, followed by washing and drying to prepare an immobilized lipoprotein film.

(3) Construction of Labeled Antibody

Anti-human hemoglobin $A_{1c}$ monoclonal antibody was adsorbed on a blue latex (manufactured by Bangs, average diameter: 0.2 μm) in a conventional manner to prepare a blue latex-labeled anti-human hemoglobin $A_{1c}$ monoclonal antibody (labeled antibody).

(4) Assay

As samples containing human hemoglobin $A_{1c}$, glycohemoglobin control levels I and II (containing 5.3% and 10.4%, respectively, of hemoglobin $A_{1c}$, both manufactured by International Reagents Corporation) were used. As a human hemoglobin $A_{1c}$-free sample, a diluted sample was prepared by diluting bovine hemoglobin (manufactured by Sigma-Aldrich Co.) with a diluent (1.25 mol/l lithium thiocyanate, 0.2 mol/l glycine, 0.25% potassium ferricyanide, pH=9.0) to give a hemoglobin concentration of 0.5 mg/ml.

The diluted sample was mixed with the blue latex-labeled antibody and allowed to react with the immobilized lipoprotein film. Four minutes thereafter, the immobilized lipoprotein film was washed and the absorbance was measured. The human albumin (manufactured by Sigma-Aldrich Co.) was added to the diluted sample to give a concentration of 0.083 mg/ml or 0.83 mg/ml (10 times higher than the hemoglobin level in normal human blood) and the same treatment was carried out.

(5) Results

The results are shown in FIG. 1. In FIG. 1, the absorbance stands for the amount of the blue latex bonded to the immobilized lipoprotein film, i.e., indicating the human hemoglobin $A_{1c}$ bonded to the immobilized lipoprotein film. The absorbance corresponds to the human hemoglobin $A_{1c}$ content, which means that human hemoglobin. $A_{1c}$ can be assayed thereby. Also, in FIG. 1, the symbols, square, lozenge and triangle, correspond to the results in the control level I, control level II and bovine hemoglobin, respectively. As is clearly shown in FIG. 1, the absorbance remains constant regardless of the concentration of the human albumin added.

EXAMPLE 3

The steps in Example 1 were carried out in the same manner, except for using olive oil, linseed oil or coconut oil (each manufactured by Nacalai Tesque) as a substitute for the lipid extract in the construction of the immobilized lipoprotein film in Example 2 (2). The results are shown in Table 1 below. As is clearly shown in Table 1, absorbance corresponding to the human hemoglobin $A_{1c}$ content was obtained in each oil, which means that human hemoglobin $A_{1c}$ can be assayed thereby.

TABLE 1

| Fat sample employed ($A_{1c}$ relative content:%) | Olive oil | Linseed oil | Coconut oil |
| --- | --- | --- | --- |
| Bovine hemoglobin (0%) | 0.083 | 0.088 | 0.068 |
| Glycohemoglobin control level I (5.3%) | 0.682 | 0.395 | 0.286 |
| Glycohemoglobin control level II (10.4%) | 0.947 | 0.660 | 0.572 |

EXAMPLE 4

Correlation Test

The steps (1) to (3) in Example 2 were carried out in the same manner.

(4) Assay

A calibration curve was preliminarily formed using hemoglobin $A_{1c}$ samples with known concentrations in accordance with the assay method of Example 2 (4) using human whole blood as a sample. Then, the absorbance of the human whole blood sample was converted into the hemoglobin $A_{1c}$ content (%) and the value thus obtained was compared with the data of an HPLC method (HLC-723 G hemoglobin III type, manufactured by Tosoh Corporation).

(5) Results

Figure 2:
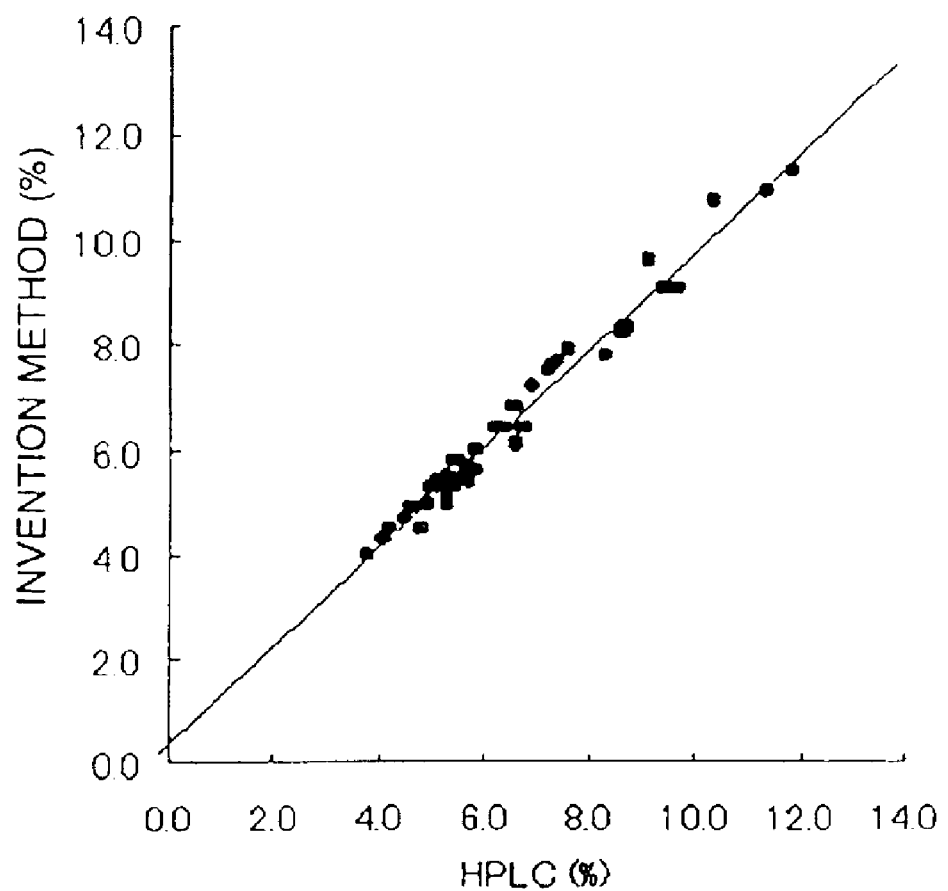
FIG. 2 is a graph showing the correlation between the method of the present invention using the lipoprotein and an HPLC method with regard to human hemoglobin $A_{1c}$.

FIG. 2 shows the correlation between these two methods.

Correlation formula $Y$ (the invention method) $=0.940 \times (HPLC) + 0.402$

Correlation coefficient $R=0.988$ $N=50$

Namely, a remarkably high correlation is observed.

This application is based on Japanese application No. 2000-213481, filed on Jun. 9, 2000, the entire content of which is incorporated herein by reference.

While the invention has been described in detail and with reference to specific embodiments thereof, it will be apparent to one skilled in the art that various changes and modifications can be made therein without departing from the spirit and scope thereof. All references cited herein are incorporated, by reference, in their entirety.

What is claimed is:

1. A method of assaying hemoglobin or a hemoglobin analogue in a sample, comprising reacting the sample with a lipoprotein to form a selective complex of the lipoprotein with hemoglobin or a hemoglobin analogue in the sample, and then determining the amount of the complex formed to assay the hemoglobin or a hemoglobin analogue in a sample.

2. The method according to claim 1, wherein the lipoprotein is a soluble lipoprotein.

3. The method according to claim 1, wherein the lipoprotein comprises a lipid and a protein.

4. The method according to claim 3, wherein the lipid is a lipid extracted from a specimen containing a protein.

5. The method according to claim 3, wherein the lipid is a lipid containing fatty acid side chains differing from each other in carbon atom number or unsaturation degree.

6. The method according to claim 3, wherein the lipid comprises a triglyceride.

7. The method according to claim 1, wherein the assayed hemoglobin or hemoglobin analogue is glycohemoglobin.

* * * * *